United States Patent [19]

Kohno

[11] Patent Number: 4,999,511
[45] Date of Patent: Mar. 12, 1991

[54] SURFACE STATE INSPECTING DEVICE FOR INSPECTING THE STATE OF PARALLEL FIRST AND SECOND SURFACES

[75] Inventor: Michio Kohno, Tokyo, Japan

[73] Assignee: Canon Kabushiki Kaisha, Tokyo, Japan

[21] Appl. No.: 493,438

[22] Filed: Mar. 14, 1990

[30] Foreign Application Priority Data

Mar. 15, 1989 [JP] Japan .................................. 1-064777
Feb. 21, 1990 [JP] Japan .................................. 2-040219

[51] Int. Cl.⁵ ...................... G01N 21/88; G01N 21/89
[52] U.S. Cl. ...................................... 250/572; 356/237
[58] Field of Search .............................. 250/559–563, 250/571, 572; 356/237, 239, 338, 429–431, 445

[56] References Cited

U.S. PATENT DOCUMENTS

| | | | |
|---|---|---|---|
| 4,431,299 | 2/1984 | Matsui et al. | 355/8 |
| 4,460,273 | 7/1984 | Koizumi et al. | 250/563 |
| 4,468,120 | 8/1984 | Tanimoto et al. | 250/572 |
| 4,669,875 | 6/1987 | Shiba et al. | 250/572 |
| 4,779,988 | 10/1988 | Horiguchi | 250/572 |
| 4,886,975 | 12/1989 | Murakami et al. | 250/572 |

FOREIGN PATENT DOCUMENTS

| | | |
|---|---|---|
| 179641 | 8/1987 | Japan . |
| 188949 | 8/1987 | Japan . |
| 219631 | 9/1987 | Japan . |
| 274247 | 11/1987 | Japan . |
| 274248 | 11/1987 | Japan . |

Primary Examiner—David C. Nelms
Assistant Examiner—Stephone B. Allen
Attorney, Agent, or Firm—Fitzpatrick, Cella, Harper & Scinto

[57] ABSTRACT

A surface state inspecting device, usable with a sample having substantially parallel first and second surfaces coupled by a side wall, for inspecting the state of each of the surfaces, is disclosed. The device includes a light irradiating system for projecting light obliquely to the sample, from the first surface side; an inspecting system for receiving light from the first surface irradiated by the irradiating system and light from the second surface irradiated with the light passed through the first surface, for inspecting the first and second surfaces; and an inspection control system effective to set a time zone for inspection of the first surface so that it does not overlap with the moment at which light impinges on a boundary between the second surface and the side wall.

15 Claims, 12 Drawing Sheets

SURFACE STATE INSPECTING DEVICE FOR INSPECTING THE STATE OF PARALLEL FIRST AND SECOND SURFACES

FIELD OF THE INVENTION AND RELATED ART

This invention relates to a device for inspecting the state of a surface of an article and, more particularly, to a surface state inspecting device for inspecting any foreign particles adhered to the surface of a substance such as a glass plate covered by a dust-shielding transparent protection film (pellicle film).

The photolithographic process is one major process of manufacture of semiconductor devices. This process uses an original, called a "reticle", having a circuit pattern formed by patterning the surface of a silica glass plate with a non-transparent material such as chromium or chromium oxide. By irradiating the reticle with ultraviolet light from above and by projecting the reticle onto the surface of a resist-coated wafer in a reduced scale through a printing lens having super resolution, a desired circuit pattern can be formed on the wafer as a chip. By moving stepwise a stage which carries thereon the wafer, plural chips can be formed on the wafer, repeatedly. If, however, a piece of dust is likewise present on the reticle, it is image-transferred onto the wafer. Thus, an image of such an unwanted foreign particle is reproduced in every chip of the wafer, resulting in a possibility that all the chips are defective.

In order to prevent adhesion of foreign particles to a reticle, use of a pellicle film has been proposed. The pellicle film is a thin film made of a material having a high light transmissibility, such as nitrocellulose, for example, and usually two pellicle films are adhered to a reticle with spacings of 4–10 mm, to both faces of the reticle substrate. The outer periphery of the pellicle film is supported by a metal frame member made of an aluminum alloy, for example. Before a reticle is used for printing, the surface state of the reticle is inspected and, thereafter, pellicle films are adhered to it. Nevertheless, just before execution of the printing, it is necessary to perform the foreign-particle inspection to the four surfaces (i.e. the upper pellicle surface, the lower pellicle surface, the patterned surface of the substrate which is usually the lower surface of the substrate, and the non-patterned opposite surface of the substrate (glass blank surface) which is usually the upper surface). This is because: with regard to the reticle substrate surfaces, there is a sufficient possibility that foreign particles are adhered to them during the pellicle attaching operation and, with regard to the upper and lower pellicle surfaces on the other hand, although a small foreign particle adhered to the pellicle surface may not directly be imaged on the wafer, a large foreign particle can block the printing light, causing a corresponding non-uniformness in illuminance. This may result in the formation of defective wiring of a circuit due to insufficient exposure and thus result in the production of defective articles.

As a proposal having been made in an attempt to solve such a problem, there is an inspecting device wherein a laser beam 1 is inputted to a reticle obliquely from above in order to reduce as much as possible a pattern signal from the pattern surface to thereby increase the signal-to-noise ratio with respect to a foreign-particle signal, wherein four light receiving optical systems which are focused to the four surfaces, respectively, are provided to allow simultaneously inspection of the four surfaces, and wherein the laser beam is scanningly deflected in a predetermined direction by a rotating means such as a polygonal mirror while, on the other hand, a stage is moved in a direction perpendicular to the predetermined direction, whereby the reticle surface is inspected two-dimensionally. Such an inspecting apparatus is disclosed in Japanese Laid-Open Patent Applications, Laid-Open Nos. Sho 62-188949, Sho 62-219631, Sho 62-274247 and Sho 62-274248.

If, as described, the system is arranged to inspect four surfaces at the same time with the provision of light receiving optical systems for the respective surfaces to be inspected and when a laser beam is inputted obliquely, as illustrated in FIG. 1 at a certain time, the laser beam is blocked by a pellicle frame $F_P$, with a result that the laser beam 1 does not impinge on a zone of the blank surface of the reticle L, of a length $L_B$ from the edge of the frame to the point B, a zone of the pattern bearing surface of a length $L_C$ to the point C, and a zone of a lower pellicle P surface of a length $L_D$ to the point D. Consequently, detection is not attainable with regard to these zones.

In an attempt to solve such a problem, namely, in an attempt to allow inspection of a partion close to the pellicle frame, there has been proposed an inspecting device wherein a stage for holding a reticle L is rectilinearly displaced in the direction of an arrow S in FIG. 1 to perform inspection of a right-hand half of the reticle surface as viewed in FIG. 1 and, thereafter, the stage is returned and the reticle is rotated by 180 degrees, and wherein the stage is then similarly rectilinearly displaced again to perform inspection of the left-hand half of the reticle as viewed in FIG. 1. Such an inspecting device is disclosed in Japanese Laid-Open Patent Application, Laid-Open No. Sho 62-179641.

Actually, however, even with use of such an inspecting device, it is difficult to perform the inspection up to the very edge of to the inside surface of the pellicle frame. This is because of a flare which might be caused when the laser beam impinges on the surface of adhesion between the pellicle frame and the reticle glass surface. This will be explained with reference to FIG. 2.

In the drawing, reference characters $D_{T1}$, $D_{T2}$, $D_{T3}$ and $D_{T4}$ denote photoreceptors which are provided to detect scattered lights from the upper pellicle surface, the reticle upper surface, the reticle lower surface and the lower pellicle surface, respectively, while reference characters $O_{P1}$, $O_{P2}$, $O_{P3}$ and $O_{P4}$ denote light receiving optical systems which are provided to guide the scattered lights from the corresponding surfaces to the corresponding photoreceptors $D_{T1}$, $D_{T2}$, $D_{T3}$ and $D_{T4}$. As a stage which holds the reticle moves rectilinearly and leftwardly as viewed in the drawing, the laser beam displaces relatively rightwardly along the reticle and, finally, it impinges on the cemented part of an upper pellicle frame and the glass surface. Usually, such a cemented part comprises a duplex adhesive tape and a sponge layer (about 1 mm in thickness). Therefore, when the laser beam impinges thereat, the light is irregularly reflected such that scattered light advances omnidirectionally. The quantity of such scattered light is remarkably large, as compared with the diameter of a smallest foreign particle to be detected by this type of inspecting device (the diameter being 1–2 microns for the pattern bearing surface; about 5 microns for the glass surface; and not less than 20 microns for the pellicle surface). A portion of such scattered light is reflected by the upper pellicle surface and, after being reflected by the glass surface, it goes along the optical axis of the light receiving optical system $O_{P1}$ for the upper pellicle surface, which is inclined toward the light 1 entrance side with respect to a normal to the pellicle surface at the point A', and finally it enters into this optical system. If this occurs, the photoreceptor $D_{T1}$ may operate to erroneously detect as if that a foreign particle is present at the position A' on the upper pellicle surface.

Another example of erroneous detection with the upper pellicle surface detecting system will be explained with reference to FIG. 3. What is illustrated in FIG. 3 is a case wherein, as the stage moves rectilinearly and leftwardly as viewed in the drawing, like the FIG. 2 example, the beam passes through the reticle and impinges on the edge portion D" of the lower pellicle frame. Usually, the edge portion of the pellicle frame $F_P$ is provided by a rough surface of an aluminum alloy, such that when a beam impinges thereat, the light is irregularly reflected. Here, the intensity of the scattered light is stronger than that from the cemented part. A portion of such scattered light may enter into the light receiving system for the upper pellicle surface and impinge against the surface of the inside wall of the light receiving system $O_{P1}$, such that a secondary flare producing source is defined thereat. If a field stop is added to the light receiving system so that only the light advancing along and in the neighborhood of the light reception optical axis of the light receiving system $O_{P1}$ can pass therethrough, once such an intense flare is produced within the light receiving system, a portion thereof can impinge upon a photomultiplier and erroneous detection may be made, as if a foreign particle is present at the position A".

As seen from FIG. 2, with regard to the light receiving means (in this example, it comprises the light receiving system $O_{P1}$ and the photoreceptor $D_{T1}$) for inspecting the pellicle which is on the side on which the light 1 is projected at first (in this example, the upper side as viewed in the drawing), the detection point A' is on a side opposite to the direction of advancement of the obliquely inputted light 1 (in this example, the left-hand side as viewed in the drawing), as compared with the other detection point such as at B'. For this reason, this light receiving means is disposed on a side (the left-hand side in the drawing) opposite to the direction of advancement of the obliquely inputted light 1, as compared with the other light receiving means ($O_{P2}$ and $D_{T2}$; $O_{P3}$ and $D_{T3}$; $O_{P4}$ and $D_{T4}$). Accordingly, every time such flare is produced, this light receiving means is in an operative state for inspection. Further, since the other light receiving means is disposed on the side (right-hand side in the drawing) which is in the direction of advancement of the obliquely inputted light 1, in many cases, from the space factor, the optical axis of the light receiving system ($O_{P1}$) is set to be inclined toward the light 1 (leftwardly in the drawing) with respect to a normal to the pellicle. Accordingly, there is a particularly high possibility of erroneous detection due to the above-described flare, in relation to the pellicle inspecting photoreceptor ($D_{T1}$ in this example) which is on the side (upper side in the drawing) on which the light is projected first.

SUMMARY OF THE INVENTION

It is accordingly a primary object of the present invention to provide a surface state inspecting method and device which assures inspection less affected by the effect of flare caused by a pellicle frame or the like.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 5:
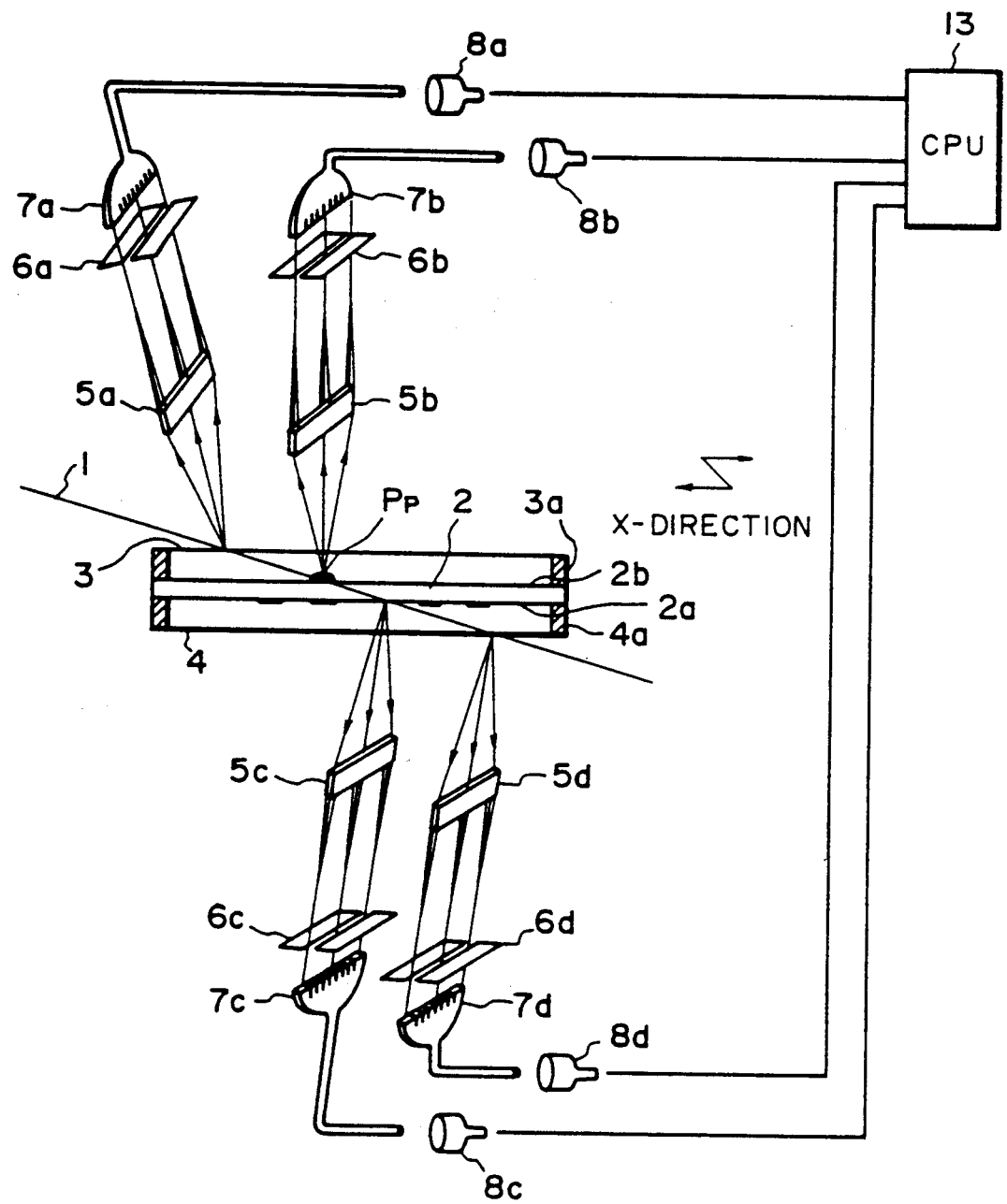
FIG. 5 is a schematic view of an optical arrangement of the first embodiment.
Figure 6:
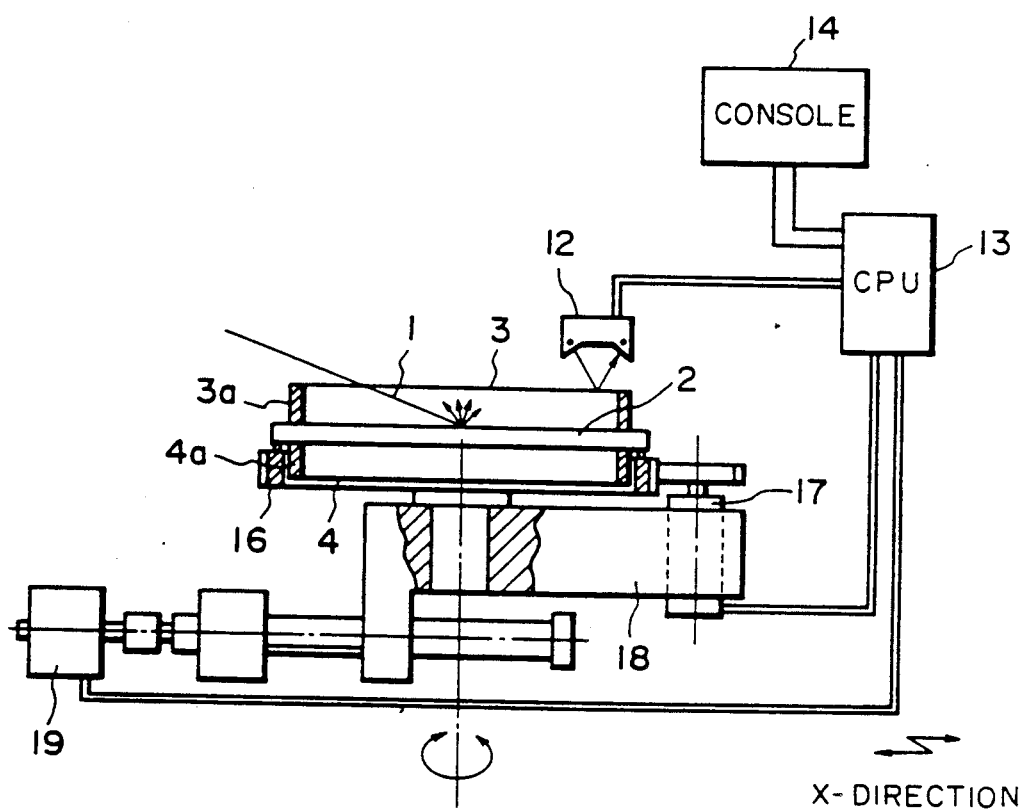
FIG. 6 is a schematic view of a driving system of the first embodiment.

FIGS. 4A through 4G are schematic representations for explaining the operation of a surface state inspecting device according to a first embodiment of the present invention. FIG. 5 illustrates an optical arrangement of the inspecting device, and FIG. 6 illustrates a driving system of the inspecting device.

Denoted in these drawings at 1 is a light beam supplied from a laser (light source), not shown, which is scanningly deflected in a direction perpendicular to the sheet of the drawing by a scanning means (also not shown) such as a polygonal mirror or the like. Denoted at 2 is a substance such as a reticle, for example, which is a subject to be examined. Numerals 2a and 2b denote upper and lower surfaces of the substance 2, respectively. Numerals 3 and 4 denote pellicle protecting films, respectively, for protecting the substance 2. Numerals 3a and 4a denote pellicle frames for holding the pellicle protecting films 3 and 4, respectively.

Denoted in FIG. 5 at 5a–5d are optical members each having a plurality of Selfoc lenses arrayed one-dimensionally ("Selfoc" is a registered trade mark owned by Nippon Itagarasu Kabushiki Kaisha, Japan). These optical members 5a–5d are set to be focused upon the surfaces 3, 2b, 2a and 4 to be examined, respectively. Denoted at 6a–6d are field stops each being disposed close to a position which is optically conjugate with a corresponding surface to be examined, with respect to a corresponding one of the optical members 5a–5d. Denoted at 7a–7d are light guides for directing the lights passed through the respective field stops 6a–6d to photoreceptors 8a–8d, respectively. Output signals of the photoreceptors 8a–8d are inputted to a central processing unit (CPU) 13 in which the presence/absence of any foreign particle is examined. As will be described later, in the CPU 13, the position on each surface currently being illuminated by the light beam is continuously calculated and, as a result, the position of any foreign particle upon each surface can be measured. The optical member 5b has an optical axis which is set substantially parallel to a normal to the substance in order to assure that the optical member 5b does not easily receive flare light as described hereinbefore. On the other hand, each of the optical members 5a, 5c and 5d has an optical axis which is inclined to the side of the light beam 1 (leftwardly as viewed in the drawing), with respect to a normal to the surface to be examined, at the point of inspection.

In the present embodiment, the optical member 5a, the field stop 6a, the light guide 7a and the photoreceptor 8a cooperate to provide a part of one detecting means (A). Similarly, the remaining optical members 5b–5d, field stops 6b–6d, light guides 7b–7d and photoreceptors 8b–8d constitute respective parts of respective detecting means (B, C and D).

It is now assumed that a foreign particle $P_p$ such as a piece of dust, for example, lies on the surface 2b to be examined. Then, as the light 1 impinges on the foreign particle $P_p$, omnidirectionally scattered light is produced from the foreign particle. Here, since the detecting means B is focused upon the surface 2b, being examined, the optical member 5b can efficiently collect the scattered light. As a result, the output of the photoreceptor 8b increases.

On the other hand, the remaining detecting means A, C and D are defocused with respect to the surface 2b being examined and, additionally, the field stops 6a, 6c and 6d are disposed close to the positions which are optically conjugate with the respective surfaces to be examined through the respective optical members 5a, 5c and 5d, and therefore, the scattered light from the foreign particle $P_p$ on the surface 2b being examined is blocked by these field stops 6a, 6c and 6d. As a result, the outputs of the photoreceptors 8a, 8c and 8d do not change.

In the present embodiment, the output signals from the four photoreceptors 8a–8d are used to detect the presence of any foreign particle on each surface being examined.

Further, each of the optical members 5a–5d comprises Selfoc lenses arrayed one-dimensionally in accordance with the scanning direction of the light. This makes it possible to reduce the size of the light collecting part and to ensure that the scattered light from a foreign particle on a surface being examined is efficiently collected.

It is to be noted that each optical member of the present embodiment may be provided by a cylindrical lens or, alternatively, an array of bar lenses as disclosed in U.S. Pat. No. 4,431,299, in place of using Selfoc lenses.

If, in the present embodiment, the scanning light beam is so projected that it is focused on one surface such as the upper surface 2a of the substance 2, for example, on the other surfaces to be examined, the light is defocused. Generally, however, a foreign particle to be considered with regard to the pellicle surface or the lower surface 2b of the substance 2 is larger than a foreign particle to be considered with regard to the upper surface 2a of the substance 2. Therefore, good detecting precision is easily obtainable without repeating the measurement by focusing the light to each surface to be examined.

Referring to FIG. 6, a driving system will be explained. FIG. 6 illustrates a reticle 2 having pellicle protecting films 3 and 4 attached thereto as well as a sample stage 16 and a driving means 18, as viewed in a horizontal direction.

The reticle 2 as covered by the pellicle protecting films 3 and 4 through pellicle frames 3a and 4a, is placed on, and held by, the sample stage 16, and then, the stage 16 is moved in an X direction by a feeding motor 19, while being pivotably supported by the driving means 18. Simultaneously therewith, the light is scanningly deflected in a direction perpendicular to the sheet of the drawing, whereby raster scanning (two-dimensional scanning) is performed. In the device of the present embodiment, the stage 16 is pivotably supported by the driving means 18, so that it can be rotated by a motor 17. More specifically, by means of the motor 19, the sample stage 16 is driven in the X-direction and, after the inspection of a particular zone is completed, the sample stage 16 is rotated through 180 degrees by means of the motor 17 provided in the driving means 18. Subsequently, the motor 19 is reversed to drive the stage 16 in a direction opposite to the direction of the drive made initially, whereby the stage 16 is returned to the inspection start position. Then, the inspection of another zone of each surface is initiated.

If the reticle is not provided with the pellicle protecting films 3 and 4, as a matter of course, it is not necessary to rotate the reticle 2. Accordingly, a reflection type sensor 12 is provided to detect the presence/absence of the pellicle protecting films 3 and 4 and, in the CPU 13, the necessity of rotation is discriminated. Further, even if the reticle 2 is provided with the pellicle protecting films 3 and 4, the range of inspection can be designated at a console 14 and, in the CPU 13, whether or not the inspection to the designated range of inspection is attainable without actuating the reticle rotating mechanism, can be discriminated. On the basis of the results of such discrimination, the motors 17 and 19 operate selectively in accordance with the discriminations. The position of the stage 16 is monitored by a detecting means (not shown) such as an encoder, for example, and it is transmitted to the CPU. Also, the current position of the scanning beam 1 is continuously monitored through the CPU, by monitoring the state of operation of a light scanning means (not shown). As the reticle is correctly positioned on the stage 16 by a positioning means (not shown) with the information concerning the pellicle frame mounting position being inputted to the CPU beforehand, in the CPU 13, the position on each surface currently being illuminated, i.e., the position being inspected, can be calculated from the position of the stage 16, the position of the scanning beam 1, the information of the reticle position and the information of the pellicle frame mounting position.

In FIGS. 4A through 4G, the sequential operation for inspecting these four surfaces in accordance with the concepts of the present invention is illustrated. Reference characters $E_L$ and $E_R$ denote the left-hand and right-hand ends of the reticle 2 as viewed in FIG. 4A. The sequence of operation will be explained below.

Figure 1:
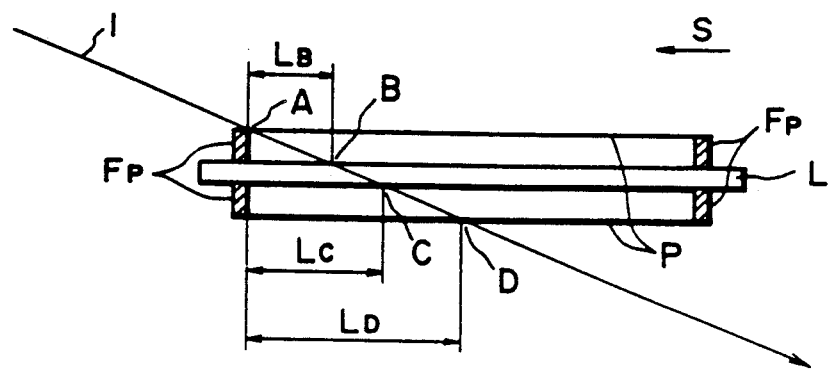
FIGS. 1 through 3 are schematic views, for explaining the inconveniences involved in conventional inspecting devices.
Figure 2:
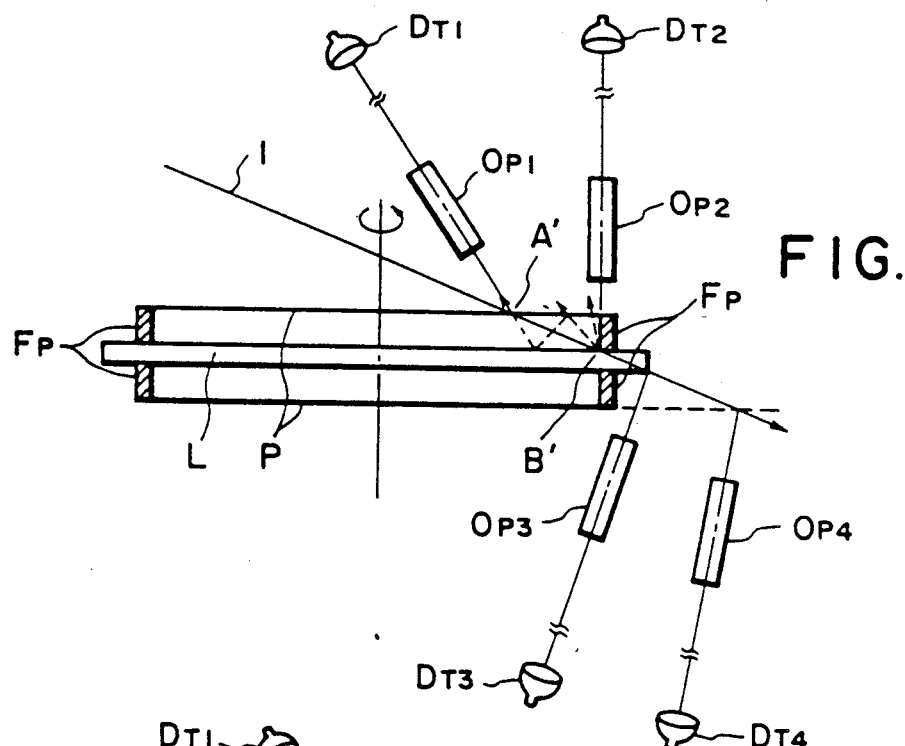
Figure 3:
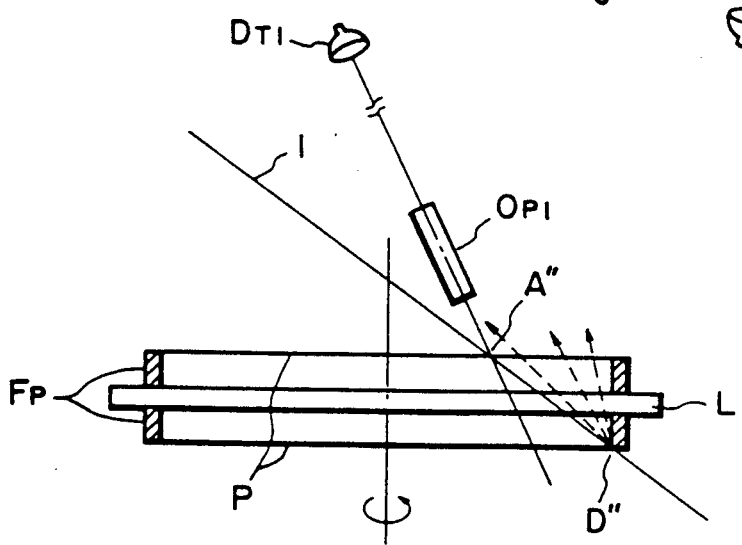
Figure 4:
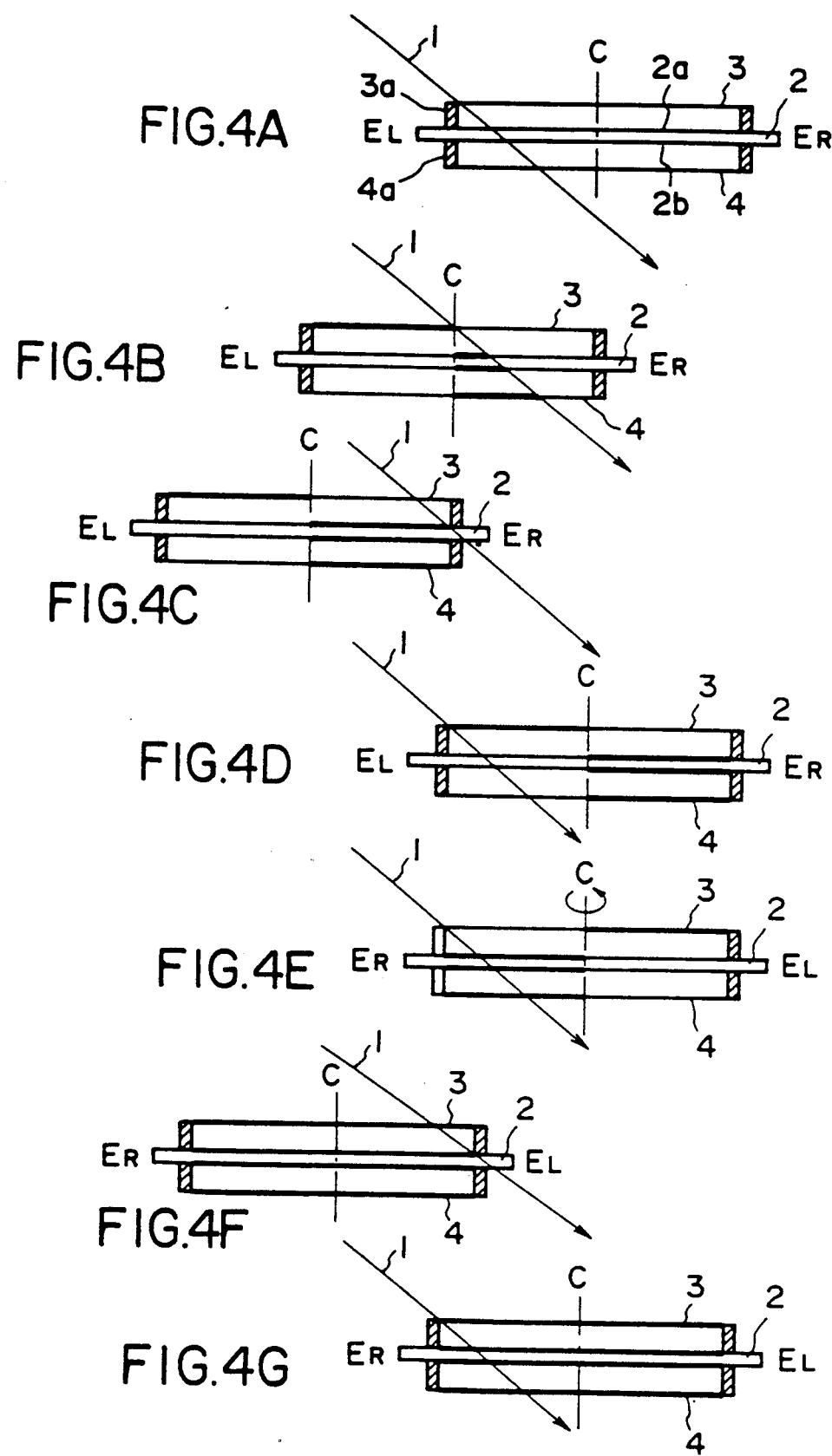
FIGS. 4A through 4G represent schematic views, for explaining the operation of a surface state inspecting device according to a first embodiment of the present invention.

(A) First, by means of the stage 16, the reticle is positioned into the inspection starting state as illustrated in FIG. 4A. The light beam is inputted from the upper left to the lower right in the drawing, and the beam 1 impinges against the left-hand edge of the upper pellicle surface 3. This is the state as illustrated. It is to be noted that the beam is being scanned in a direction perpendicular to the sheet of the drawing. Also, the angle of incidence of the beam 1 is set so that, in the illustrated state, the position of incidence upon the lower pellicle 4 is on the left-hand side of the center C of the pellicle film, as viewed in the drawing.

(B) Then, from the state (A), the stage is moved leftwardly to the position shown in FIG. 4B. With this movement, the beam 1 displaces from the left to the right along each surface. During this movement, the output of each photoreceptor is detected by the CPU 13 and, as a result, the zones as depicted by thick lines are inspected. It is to be noted here that the zones as depicted by thin lines, even after the scan, are those to be inspected during the motion (E)-(F) as will be described later. It is seen from the drawing that, during the first inspection, those parts of the upper and lower surfaces of the substrate 2 and of the lower pellicle 4 surface, which parts are on the right-hand side of the pellicle film center C as viewed in the drawing and which include no area as light-blocked by the upper pellicle frame 3a, are inspected. As compared therewith, with regard to the upper pellicle 3 surface, such portion thereof which is on the left-hand side of the pellicle center C in the drawing and to which the beam scanning is completed before the edge portion of the lower pellicle frame as well as the cemented part between the pellicle frame and the reticle 2 are scanned with the beam, is inspected. With regard to each surface, whether or not the scanning beam 1 comes to the pellicle film center and/or the inspection start point or the inspection end point, can be discriminated through the CPU 13 on the basis of the position of the pellicle film center, on each surface, as inputted into the CPU beforehand as on the basis of well as the data of the monitored stage position and beam position.

(C) As the stage moves sufficiently and the beam comes to the right-hand edge of the reticle upper surface as shown in FIG. 4C, the inspection of almost all the right-hand half or left-hand half of each surface is accomplished. Here, it is important to note that, in accordance with the concepts of the present invention, with regard to the upper pellicle surface, such a zone in which no flare is produced by the impingement of a beam passed through the upper pellicle surface against the pellicle frame, namely, the left-hand half of the upper pellicle surface as viewed in the drawing, is substantially inspected. With regard to the lower pellicle surface, since the beam passing therethrough does not impinge on the pellicle frame, the right-hand half thereof is inspected.

(D) From the state of (C), the stage is moved back to the movement start position (A) as shown in FIG. 4D.

(E) From the state of (D), the reticle is rotated through 180 degrees as shown in FIG. 4E.

(F) From the state of (E), the stage is moved leftwardly again, and the beam comes to the right-hand edge of the glass surface. This is the illustrated state in FIG. 4F. During this movement, the inspection of the four surfaces is performed in a similar manner as made in (B), and the half zones not having been inspected are inspected.

(G) From the state of (F), the stage is returned to the movement start position (A). This is the illustrated state in FIG. 4G. By rotating the reticle through 180 degrees, like (E), the state of (A) is resumed.

Figure 7:
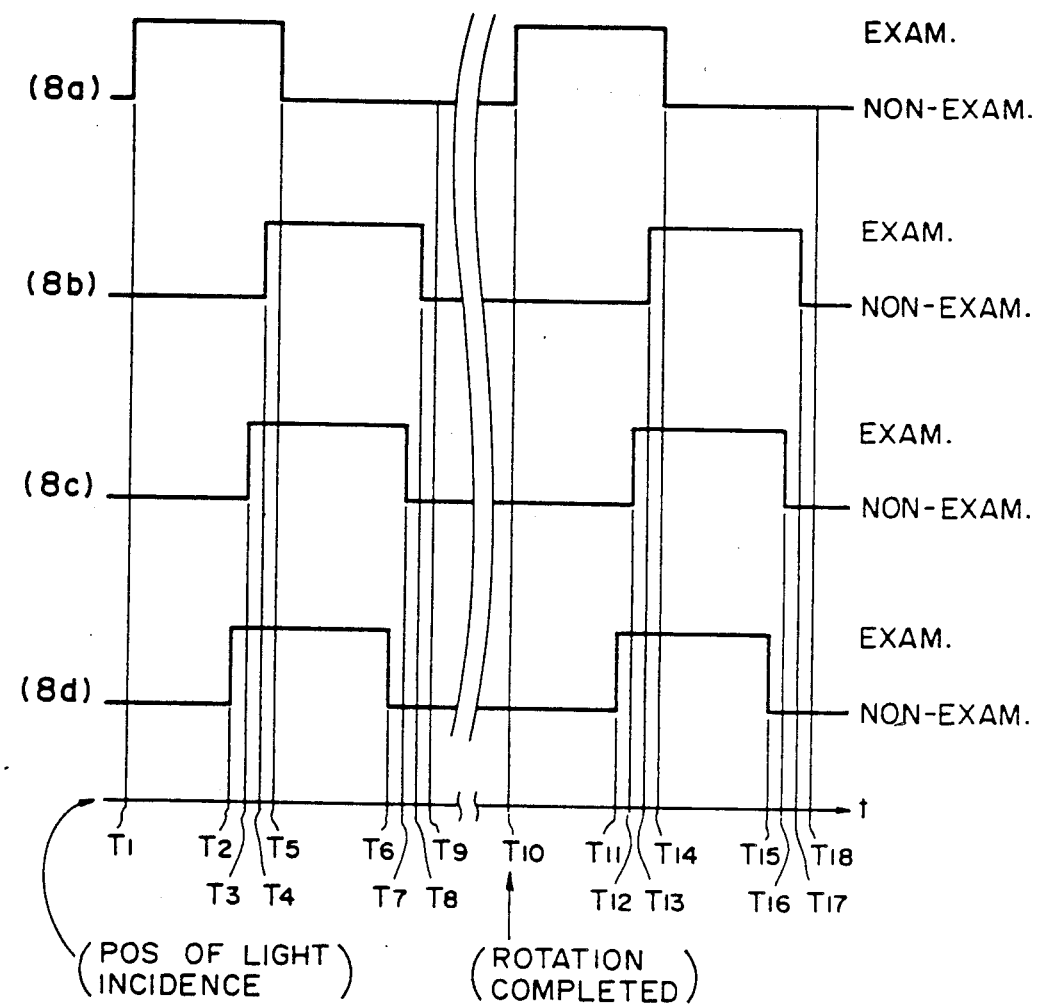
FIG. 7 is a time chart, illustrating the timing of detection through different photoreceptors.

FIG. 7 is a time chart, for explaining the manner of detection, by the CPU 13, of the outputs from the photoreceptors for execution of the inspection, in the sequence of operation described hereinbefore. From the top to the bottom of FIG. 7, the state of examination and non-examination of the CPU 13, alternating with time, to the four surfaces based on the outputs of the photoreceptors 8a–8d, is illustrated. Also, at the bottom of FIG. 7, the position of incidence of the light 1 at varying time t, is depicted as $T_1-T_{18}$. Here, $T_1$ corresponds to the end portion $E_L$ of the upper pellicle surface; $T_2$ corresponds to the central portion of the lower pellicle surface; $T_3$ corresponds to the central portion of the reticle lower surface; $T_4$ corresponds to the central portion of the reticle upper surface; $T_5$ corresponds to the central portion of the upper pellicle surface; $T_6$ corresponds to the end portion $E_R$ of the lower pellicle surface; $T_7$ corresponds to the end $E_R$ side frame contact portion of the reticle lower surface; $T_8$ corresponds to the end $E_R$ side frame contact portion of the reticle upper surface; $T_9$ corresponds to the end portion $E_R$ of the upper pellicle surface; $T_{10}$ corresponds to the end portion $E_R$ of the upper pellicle surface; $T_{11}$ corresponds to the central portion of the lower pellicle surface; $T_{12}$ corresponds to the central portion of the reticle lower surface; $T_{13}$ corresponds to the central portion of the reticle upper surface; $T_{14}$ corresponds to the central portion of the upper pellicle surface; $T_{15}$ corresponds to the end portion $E_L$ of the lower pellicle surface; $T_{16}$ corresponds to the end $E_L$ side frame contact portion of the reticle lower surface; $T_{17}$ corresponds to the end $E_L$ side frame contact portion of the reticle upper surface; and $T_{18}$ corresponds to the end portion $E_L$ of the upper pellicle surface.

Figure 14:
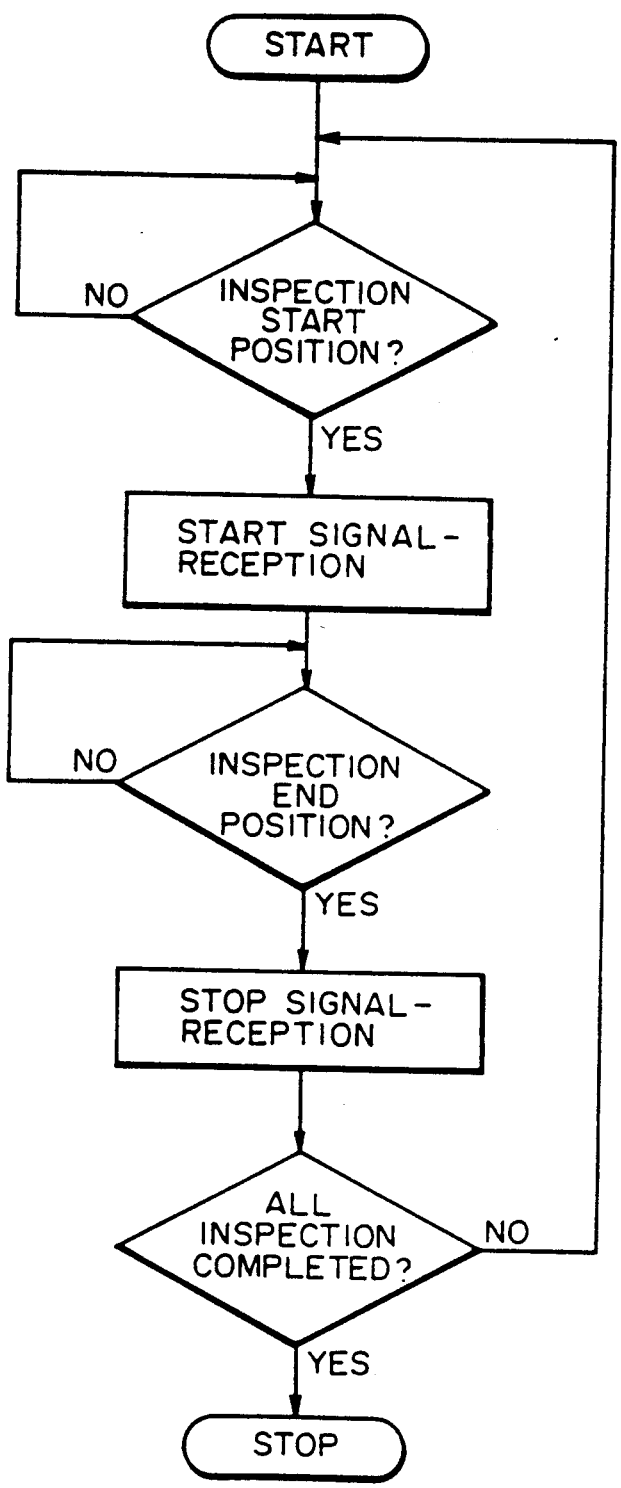
FIG. 14 is a flow chart, exemplifying the manner of detecting output signals as controlled by a CPU.

It is seen from FIG. 7 that, when the light beam 1 impinges on the contact portion ($T_7$, $T_8$, $T_{16}$, $T_{17}$) between the reticle and the pellicle frame or on the end portion ($T_6$, $T_{15}$) of the lower pellicle surface, the output of the photoreceptor 8a for inspection of the upper pellicle surface is not detected by the CPU 13. In other words, it is in a non-examination (non-inspection) state with respect to an associated surface. In accordance with the time chart shown in FIG. 7, the CPU 13 detects the outputs of the photoreceptors 8a–8d and executes the data processing for each detected output, this being made in accordance with the flow chart such as illustrated in FIG. 14.

Figure 8:
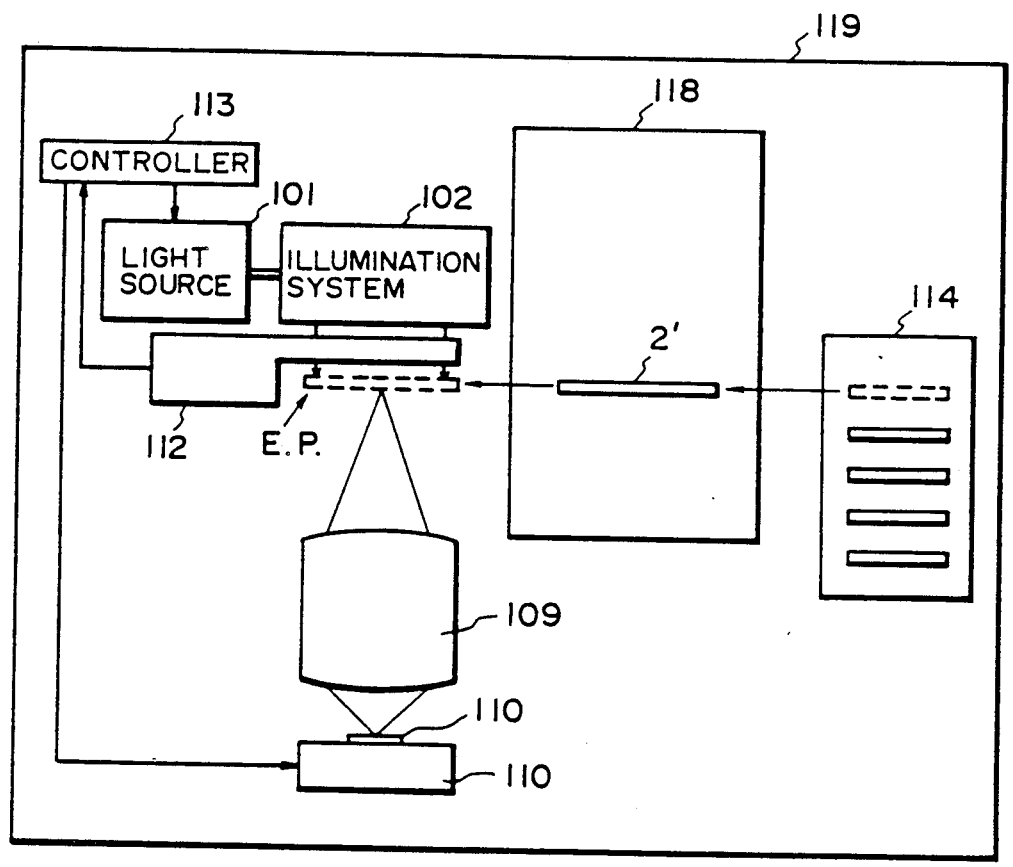
FIG. 8 is a schematic view of a general structure of a semiconductor device manufacturing exposure apparatus into which the surface state inspecting device of the first embodiment is incorporated.

FIG. 8 is a schematic view of a general structure of a semiconductor device manufacturing exposure apparatus, into which a surface state inspecting device according to the first embodiment is incorporated. Similarly, an inspecting device according to any one of the embodiments of the present invention to be described later can be incorporated into this type of exposure apparatus, in place of the first embodiment.

Denoted in FIG. 8 at 101 is a deep ultraviolet light source to be used for the exposure; at 102 is an illumination system for illuminating a reticle, placed at an exposure position E.P., with the deep ultraviolet light from the light source 101; at 109 is a projection system for projecting a pattern of the reticle as placed on the exposure position E.P. and illuminated by the illumination system; at 110 is a wafer onto which the pattern of the reticle is to be transferred; at 111 is a wafer stage for holding and positioning the wafer 110; at 112 is a position detecting device for detecting the positional relationship between the wafer 110 and the reticle as placed on the exposure position E.P.; at 113 is a controller for controlling the position of the wafer stage 111 so as to relatively align the reticle and the wafer 110 and for controlling the light emission by the light source 101; at 114 is a reticle changer for accommodating therein a plurality of reticles each having pellicle protecting films adhered thereto; at 118 is a surface state inspecting unit in which an optical arrangement such as shown in FIG. 5 as well as a driving system such as shown in FIG. 6 are accommodated; and at 119 is a chamber for accommodating therein the above-described components.

Each reticle 2' having pellicle protecting films and accommodated in the reticle changer 114 can be conveyed to the surface state inspecting unit 118 by means of a conveying device (not shown) and, in this unit, the surface state thereof can be inspected in the manner as described hereinbefore. If the reticle passes the inspection, it is conveyed to the exposure position E.P. by means of a conveying device, not shown, and the exposure of the wafer 110 with use of the reticle 2' can be made.

Figure 9A:
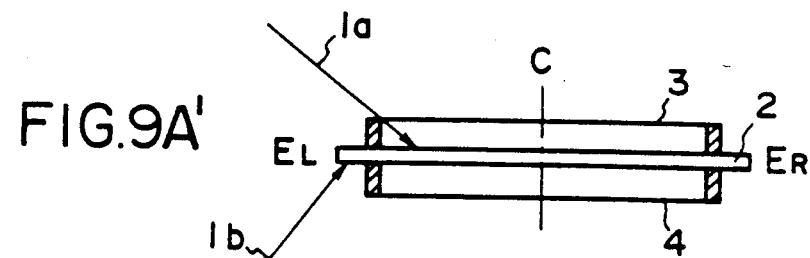
FIGS. 9A' through 9G' are schematic views for explaining the operation of a surface state inspecting device according to a second embodiment of the present invention.
Figure 10:
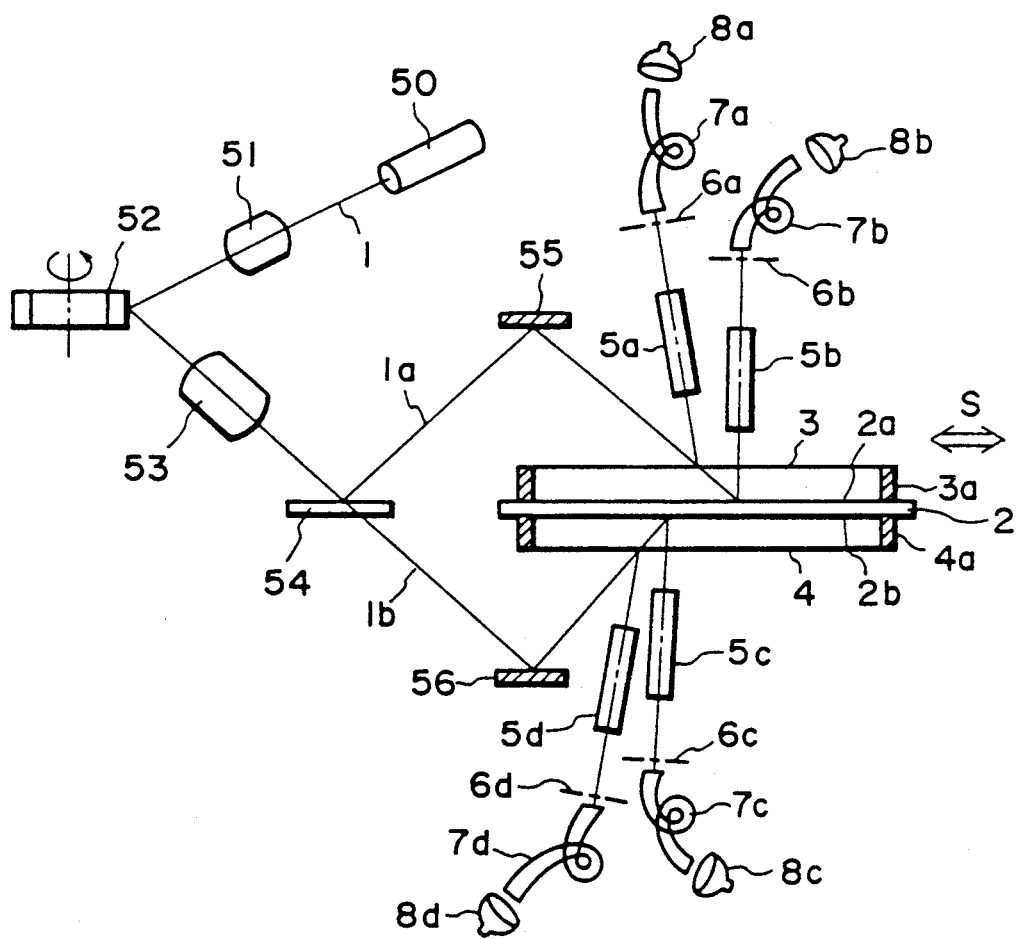
FIG. 10 is a schematic view of an optical arrangement of the second embodiment.

FIGS. 9A' through 9G' are schematic views, for explaining the operation of a surface state inspecting device according to a second embodiment of the present invention, and FIG. 10 is a schematic view of an optical arrangement of the second embodiment.

In FIG. 10, a laser beam 1 emitted from a laser tube 50 is expanded by a beam expander 51 into a predetermined beam diameter, and the expanded laser beam impinges on a polygonal mirror 52. With the rotation of the polygonal mirror 52, the laser beam is scanningly deflected in a direction perpendicular to the sheet of the drawing, and then it passes through an f-$\theta$ lens 53. After this, the laser beam is divided by a half mirror 54 into a reflected beam 1a and a transmitted beam 1b. By means of reflection mirrors 55 and 56, respectively, these laser beams are inputted to a reticle 2 obliquely from above and from below, respectively. Generally, adjustment may be made so that the upper beam is focused on a glass surface 2a while the lower beam is focused on a pattern bearing surface 2b. However, such adjustment may not be made if the particle diameter of a foreign particle to be detected is large.

Like the FIG. 5 embodiment, for each surface to be inspected, a corresponding light receiving optical system is provided, such that for each individual surface (of the four surfaces) scattered light from a foreign particle or the like can be picked up as a signal. Like FIG. 6, a stage (not shown) is used and arranged to be moved horizontally as viewed in the drawing in a timed relationship with the scan of the laser beam and, also, it is arranged to be rotatable. In the present embodiment, the scanning beam inputted from above is used for the inspection of the upper surfaces, while the scanning beam inputted from below is used to inspect the lower surfaces.

The sequence of inspection will be explained with reference to FIGS. 9A' through 9G'.

(A') By means of an unshown stage, the reticle 2 is positioned into the inspection starting state as illustrated in FIG. 9A'. In this state, the upper beam 1a impinges on the left-hand edge of the upper pellicle 3. Since, in the present embodiment, the upper beam 1a precedes the lower beam 1b, the illustrated state, is at the start point. If, on the other hand, the lower beam precedes the upper beam, the moment at which the lower beam impinges on the left-hand edge of the lower pellicle is the start point.

Figure 9B:
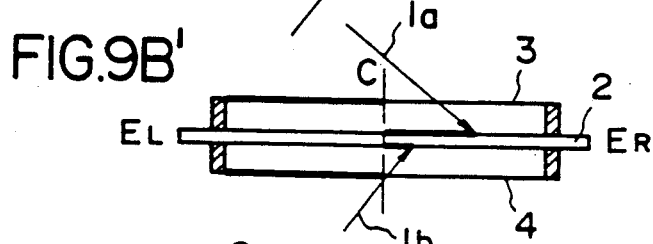
Figure 9C:
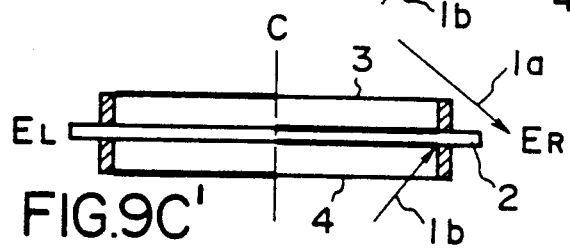
Figure 9D:
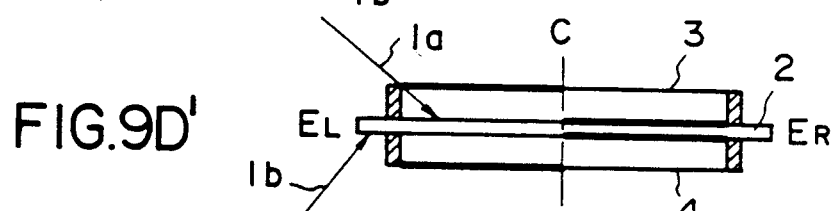
Figure 9E:
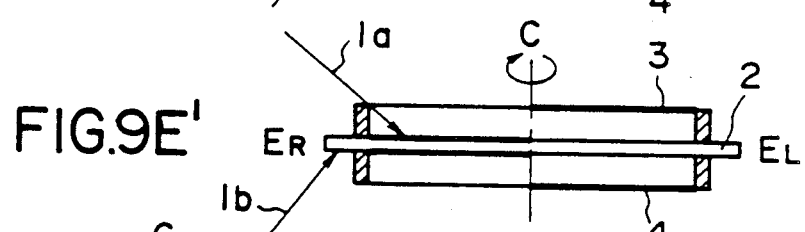
Figure 9F:
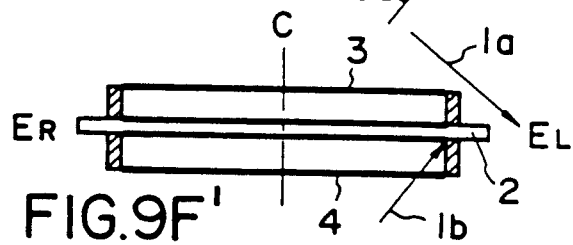
Figure 9G:
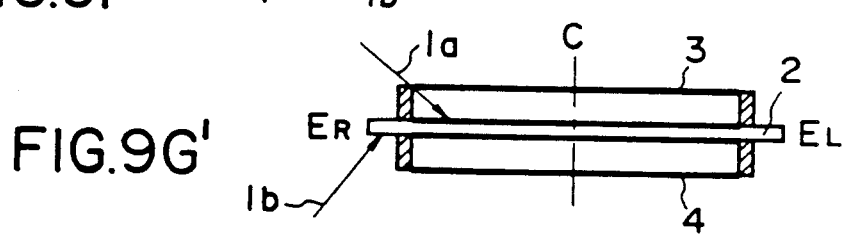

(B') From the state of (A'), the stage moves leftwardly as shown in FIG. 9B'. With this movement, the laser beams displace along the surfaces from the left to the right and, as a result, the zones as depicted by thick lines in the drawing are inspected during the movement.

(C') As the stage moves leftwardly sufficiently and the lower beam approaches the right-hand edge of the pattern bearing surface, the inspection of almost all the left-hand half of each pellicle surface as well as almost all the right-hand half of the substance is accomplished as shown in FIG. 4C'. Also in this embodiment, when the upper and lower pellicle surfaces are inspected in accordance with the concepts of the present invention, the beam passing the pellicle surface does not impinge on the pellicle frame.

(D') From the state (C'), the stage is moved rightwardly and is returned to the position (A') as shown in FIG. 4D'.

(E') From the state (D'), the reticle is rotated through 180 degrees as shown in FIG. 4E'.

(F') From the state (E'), the stage is moved leftwardly again and the lower beam comes to the righthand edge of the pattern bearing surface as shown in FIG. 4F'. During this movement, like (B'), the inspection of the four surfaces is performed, and such zones not having been inspected are inspected.

(G') From the state (F'), the stage is returned to the inspection start position (A') as shown in FIG. 4G'.

Figure 11:
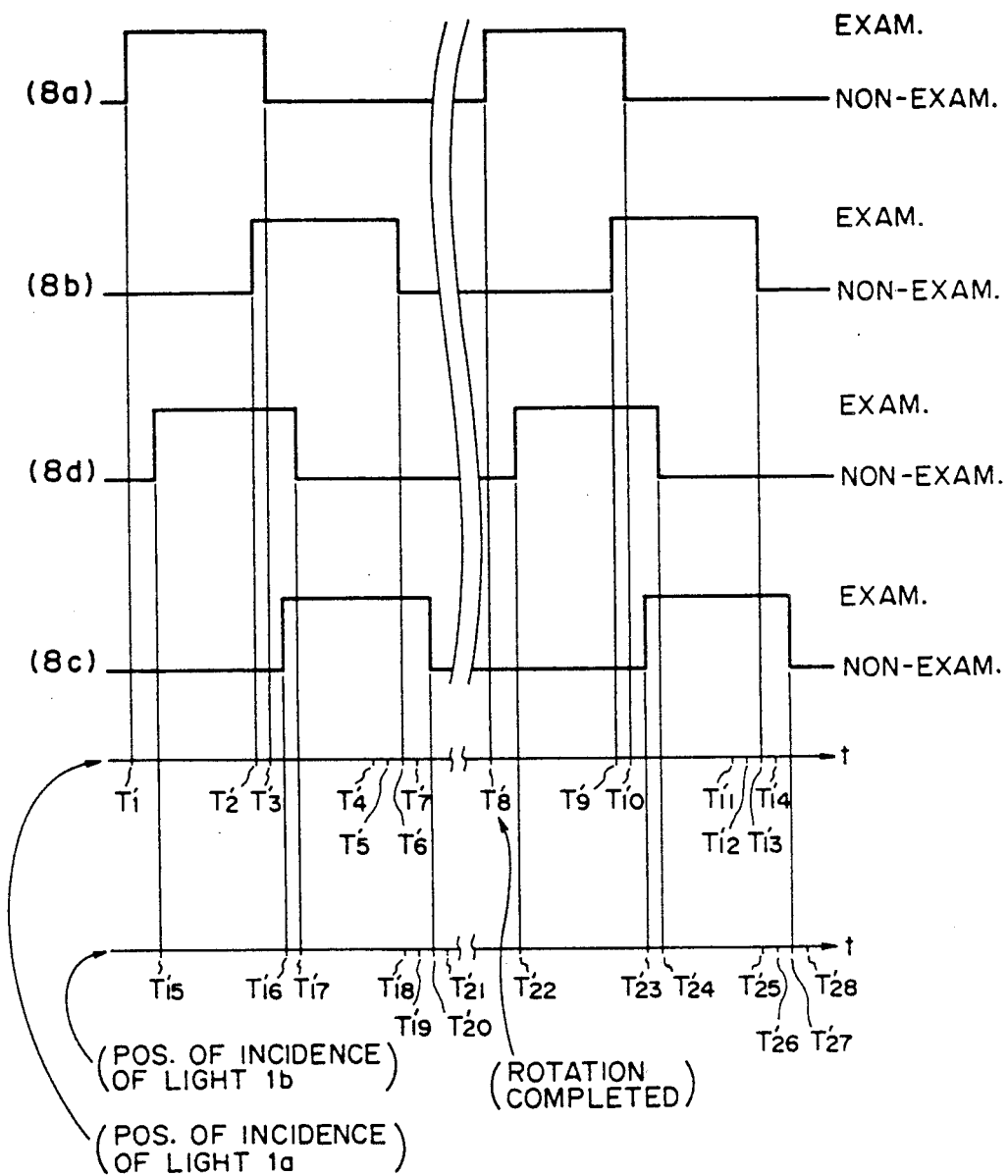
FIG. 11 is a time chart showing the timing of detection through different photoreceptors of the second embodiment.

FIG. 11 is a time chart, illustrating the manner of detection, by the CPU 13, of the outputs of the photoreceptors for execution of the inspection, in the sequence of operation as described hereinbefore. From the top to the bottom of FIG. 11, the state of examination and non-examination of the CPU 13, alternating with time, based on the outputs of the photoreceptors 8a, 8b, 8d and 8c, is illustrated. At the bottom of FIG. 11, the position of incidence of each of the light beams 1a and 1b, at varying time t, is illustrated as $T'_1-T'_{28}$. Here, $T'_1$ corresponds to the end portion $E_L$ of the upper pellicle surface; $T'_2$ corresponds to the central portion of the reticle upper surface; $T'_3$ corresponds to the central portion of the upper pellicle surface; $T'_4$ corresponds to the end portion $E_R$ of the lower pellicle surface; $T'_5$ corresponds to the end $E_R$ side frame contact portion of the reticle lower surface; $T'_6$ corresponds to the end $E_R$ side frame contact portion of the reticle upper surface; $T'_7$ corresponds to the end portion $E_R$ of the upper pellicle surface; $T'_8$ corresponds to the end portion $E_R$ of the upper pellicle surface; $T'_9$ corresponds to the central portion of the reticle upper surface; $T'_{10}$ corresponds to the central portion of the upper pellicle surface; $T'_{11}$ corresponds to the end portion $E_L$ of the lower pellicle surface; $T'_{12}$ corresponds to the end $E_L$ side frame contact portion of the reticle lower surface; $T'_{13}$ corresponds to the end $E_L$ side frame contact portion of the reticle upper surface; $T'_{14}$ corresponds to the end portion $E_L$ of the upper pellicle surface; $T'_{15}$ corresponds to the end portion $E_L$ of the lower pellicle surface; $T'_{16}$ corresponds to the central portion of the reticle lower surface; $T'_{17}$ corresponds to the central portion of the lower pellicle surface; $T'_{18}$ corresponds to the end portion $E_R$ of the upper pellicle surface; $T'_{19}$ corresponds to the end $E_R$ side frame contact portion of the reticle upper surface; $T'_{20}$ corresponds to the end $E_R$ side frame contact portion of the reticle lower surface; $T'_{21}$ corresponds to the end portion $E_R$ of the lower pellicle surface; $T'_{22}$ corresponds to the end portion $E_R$ of the lower pellicle surface; $T'_{23}$ corresponds to the central portion of the reticle lower surface; $T'_{24}$ corresponds to the central portion of the lower pellicle surface; $T'_{25}$ corresponds to the end portion $E_L$ of the upper pellicle surface; $T'_{26}$ corresponds to the end $E_L$ side frame contact portion of the reticle upper surface; $T'_{27}$ corresponds to the end $E_L$ side frame contact portion of the reticle lower surface; and $T'_{28}$ corresponds to the end portion $E_L$ of the lower pellicle surface.

It is seen from FIG. 11 that when the light beam $1a$ or $1b$ impinges on the contact portion ($T'_5$, $T'_6$, $T'_{12}$, $T'_{13}$, $T'_{19}$, $T'_{20}$, $T'_{26}$, $T'_{27}$) between the reticle and the pellicle frame, when the light $1a$ impinges on the edge portion ($T'_4$, $T'_{11}$) of the lower pellicle surface or when the light $1b$ impinges on the edge portion ($T'_{18}$, $T'_{25}$) of the upper pellicle surface, the output of the photoreceptor $8a$ for inspecting the upper pellicle surface or the output of the photoreceptor $8b$ for inspecting the lower pellicle surface is not detected by the CPU 13. Namely, it is in a non-examination (non-inspection) state with respect to an associated surface. Detection of the output of each photoreceptor by the CPU ma be made in the same manner as illustrated in the flow chart of FIG. 14.

Figure 12A:
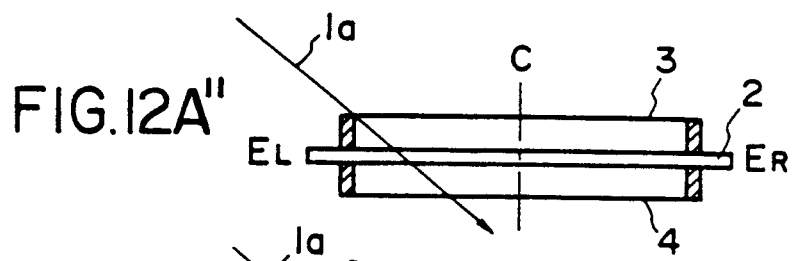
FIGS. 12A" through 12F" are schematic views for illustrating the operation of a surface state inspecting device according to a third embodiment of the present invention.

FIGS. 12A" through 12F" are schematic views for explaining the operation of a surface state inspecting device according to a third embodiment of the present invention. The optical arrangement of this embodiment is such a system wherein the half mirror 54 in the FIG. 10 arrangement is replaced by a non-transparent mirror which is retractably insertable into the path of the light.

The sequence of operation will be explained, with reference to FIGS. 12A" through 12F".

(A") By means of an unshown stage, the reticle 2 is positioned into the inspection starting state as illustrated in FIG. 12A". In this state, the beam $1a$ is projected obliquely from the upper left and impinges on the lefthand edge of the upper pellicle 3 surface.

Figure 12B:
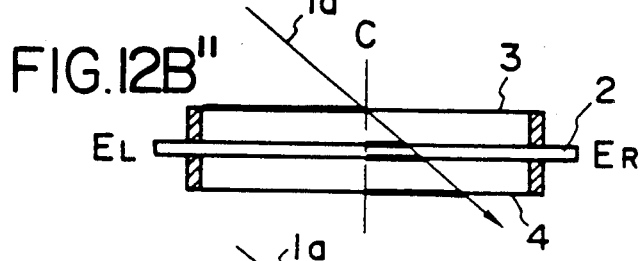

(B") From the state (A"), the stage moves leftwardly as shown in FIG. 12B". With this movement, the beam $1a$ displaces along the surfaces from the left to the right, and during this movement, the zones as depicted by thick lines are inspected.

Figure 12C:
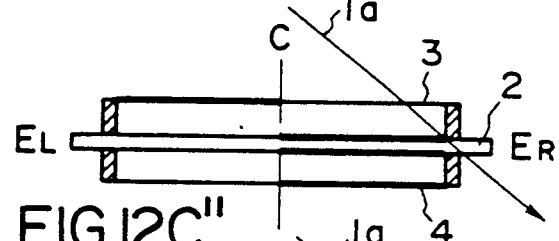

(C") As the stage moves sufficiently leftwardly and the beam $1a$ comes to the right-hand edge of the glass surface, like the state of (C) of FIG. 4C, the inspection of all the right-hand or left-hand half of each surface is accomplished as shown in FIG. 12C".

Figure 12D:
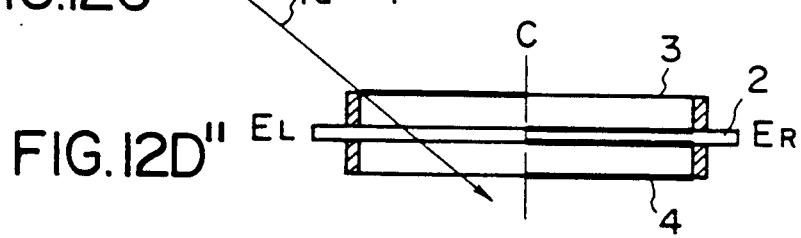

(D") From the state (C), the stage is moved rightwardly, back to its start position as shown in FIG. 12D".

Figure 12E:
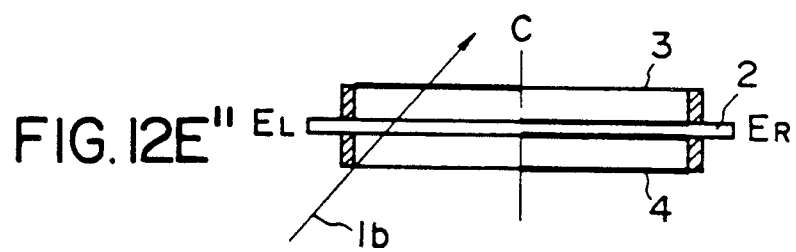

(E") The mirror, which is at the position of the half mirror 54 in FIG. 10, is retracted out of the path of light, and the beam $1b$ is inputted to the reticle obliquely from below, and the stage is moved so that the beam impinges on the left-hand edge of the lower pellicle 4 surface as shown in FIG. 12E".

Figure 12F:
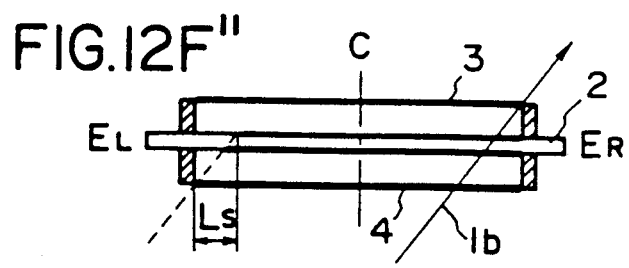

(F") The stage is moved leftwardly again for inspection of the zones not having been inspected (i.e. the right-hand half of the upper pellicle and the lefthand halves of the other three surfaces) as shown in FIG. 12F". As the beam displaces sufficiently leftwardly and comes to the right-hand edge of the upper pellicle surface, the inspection is completed.

Figure 13:
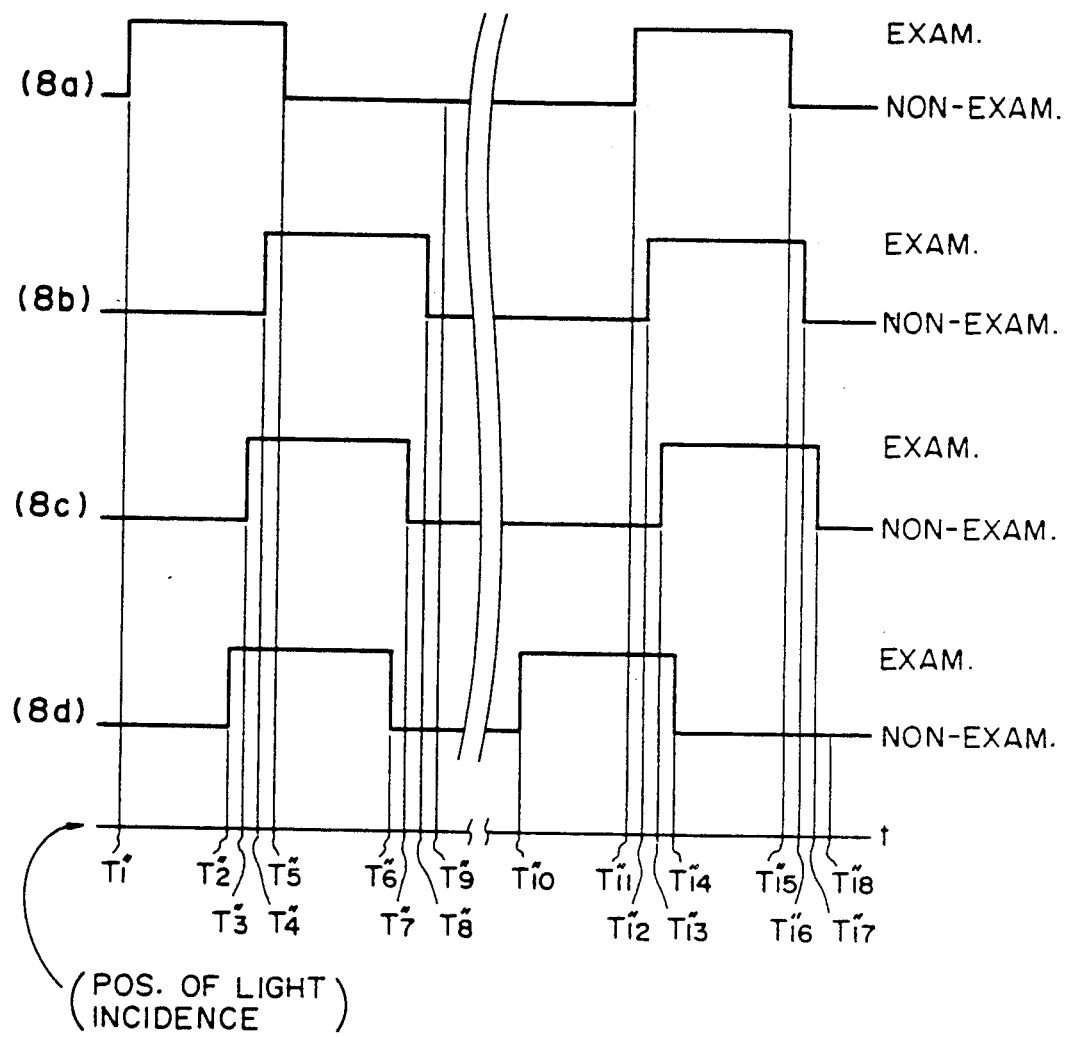
FIG. 13 is a time chart, illustrating the timing of detection through different photoreceptors of the third embodiment.

FIG. 13 is a flow chart for explaining the manner of detection, by the CPU 13, of the outputs of the photoreceptors for execution of the inspection, in the sequence of operation as described hereinbefore. From the top to the bottom of FIG. 13, the state of examination (inspection) and non-examination (non-inspection) of the CPU 13, alternating with time, based on the output of the photoreceptors $8a$–$8d$, is illustrated. At the bottom of FIG. 13, the position of incidence of the light at a varying time is illustrated as $T''_1$–$T''_{18}$. Here, $T''_1$ corresponds to the end portion $E_L$ of the upper pellicle surface; $T''_2$ corresponds to the central portion of the lower pellicle surface; $T''_3$ corresponds to the central portion of the reticle lower surface; $T''_4$ corresponds to the central portion of the reticle upper surface; $T''_5$ corresponds to the central portion of the upper pellicle surface; $T''_6$ corresponds to the end portion $E_R$ of the lower pellicle surface; $T''_7$ corresponds to the end $E_R$ side frame contact portion of the reticle lower surface; $T''_8$ corresponds to the end $E_R$ side frame contact portion of the reticle upper surface; $T''_9$ corresponds to the end portion $E_R$ of the upper pellicle surface; $T''_{10}$ corresponds to the end portion $E_R$ of the lower pellicle surface; $T''_{11}$ corresponds to the central portion of the upper pellicle surface; $T''_{12}$ corresponds to the central portion of the reticle upper surface; $T''_{13}$ corresponds to the central portion of the reticle lower surface; $T''_{14}$ corresponds to the central portion of the lower pellicle surface; $T''_{15}$ corresponds to the end portion $E_L$ of the upper pellicle surface; $T''_{16}$ corresponds to the end $E_L$ side frame contact portion of the reticle upper surface; $T''_{17}$ corresponds to the end $E_L$ side frame contact portion of the reticle lower surface; and $T''_{18}$ corresponds to the end portion $E_L$ of the lower pellicle surface.

It is seen from FIG. 13 that, when, during the scan with the light from the above, light impinges on the contact portion ($T''_7$, $T''_8$) between the reticle and the pellicle frame, or on the edge portion ($T''_6$) of the lower pellicle surface, the output of the photoreceptor $8a$ for inspecting the upper pellicle surface is not detected by the CPU 13. Thus, it is in a non-inspecting state with respect to an associated surface. Similarly, when, during the scan with the light from below, the light impinges on the contact portion ($T''_{16}$, $T''_{17}$) between the reticle and the pellicle frame or on the edge portion ($T''_{15}$) of the upper pellicle surface, the output of the photoreceptor $8d$ for inspecting the lower pellicle surface is not used for the inspection. Detection of the outputs of the photoreceptors by the CPU may be made in a similar manner as illustrated in the flow chart of FIG. 14.

In the present embodiment, the reticle is not rotated. As a result, finally there remains a region not inspected by the device, which region is at a partion as denoted by Ls) positioned on the beam input side (left-hand side, in this example) and being shaded by the pellicle frame. Since, however, at the right-hand halves, almost all the zones of the surfaces can be inspected and no reticle rotating mechanism is required (which is effective to make the device as a whole simple), the present embodiment can provide a sufficiently effective system if such a range of inspection meets the region of a circuit pattern on a reticle. As a matter of course, like the first and second embodiments, the reticle may be rotated to allow inspection of the remaining portion in a similar manner.

While in the first and second embodiments the reticle is rotated by 180 degrees after inspection of the right-hand or left-hand half of each surface being examined (A–C, A'–C') to allow inspection of the remaining zone, in place of such rotation, the beam may be switched from the left to the right, for example, so that the stage is moved only rectilinearly. On that occasion, according to the inspecting flow of the present invention, substantially the same effect is obtainable.

Also, in the above-described systems, the laser beam scanning is combined with the stage scanning movement in a direction substantially perpendicular to the laser beam scan, to thereby two-dimensionally cover the surface to be inspected. However, in place of doing so, the laser beam may be scanned two-dimensionally. The present invention is also applicable to such a case.

While the invention has been described with reference to the structures disclosed herein, it is not confined to the details set forth and this application is intended to cover such modifications or changes as may come within the purposes of the improvements or the scope of the following claims.

What is claimed is:

1. A surface state inspecting device, usable with a sample having substantially parallel first and second surfaces coupled by a side wall, for inspecting the state of each of the surfaces, said device comprising:
   irradiating means for projecting light obliquely to the sample, from the first surface side;
   inspecting means for receiving light from the first surface irradiated by said irradiating means and light from the second surface irradiated with the light passed through the first surface, for inspecting the first and second surfaces; and
   inspection control means effective to set a time zone for inspection of the first surface so that it does not overlap with the moment at which light impinges on a boundary between the second surface and the side wall.

2. A device according to claim 1, wherein said irradiating means is arranged to scan the first and second surfaces with light.

3. A device according to claim 1, further comprising rotating means for rotating the sample substantially along one of the first and second surfaces.

4. A device according to claim 3, wherein said inspection control means is effective to cause said inspecting means first to inspect a portion of the first surface near to the light irradiation side and a portion of the second surface remote from the light irradiation side, to cause said rotating means to rotate the sample through 180 degrees, and to cause said inspecting means to inspect portions of the first and second surfaces different from the portions inspected before the rotation.

5. A surface state inspecting device, usable with a sample having substantially parallel first and second surfaces coupled by a first side wall and third and fourth surfaces coupled by a second side wall and being substantially parallel to the first and second surfaces, for inspecting the state of each of the surfaces, said device comprising:
   irradiating means for projecting at least a first light obliquely to the sample, at least from the first surface side;
   inspecting means for receiving lights from the surfaces irradiated by said irradiating means to inspect the surfaces; and
   inspection control means for setting a time zone for inspection of the first surface so that it does not overlap with the moment at which the light impinges on a boundary between the second surface and the first side wall, a boundary between the third surface and the second side wall or a boundary between the fourth surface and the second side wall.

6. A device according to claim 5, wherein said irradiating means is arranged to illuminate the third and fourth surfaces with the first light passed through the first surface.

7. A device according to claim 5, wherein said irradiating means is arranged to illuminate the third and fourth surfaces by projecting the second light obliquely from the fourth surface side.

8. A device according to claim 7, wherein said irradiating means projects the first and second lights to the sample at the same time.

9. A device according to claim 7, wherein said irradiating means is arranged to selectively project the first and second lights to the sample.

10. A device according to claim 5, wherein said irradiating means is arranged to scan the first to fourth surfaces of the sample with light.

11. A device according to claim 5, further comprising rotating means for rotating the sample substantially along one of the first to fourth surfaces.

12. A device according to claim 11, wherein said inspection control means is effective to cause said inspecting means first to inspect a portion of the first surface near to the light irradiating side and a portion of the second surface remote from the light irradiation side, to cause said rotating means to rotate the sample through 180 degrees, and to cause said inspecting means to inspect portions of the first and second surfaces different from the portions inspected before the rotation.

13. An exposure apparatus, usable with a sample having substantially parallel first and second surfaces coupled by a side wall, for inspecting the state of each surface of the sample and for transferring a pattern of the sample to a workpiece, said apparatus comprising:
   irradiating means for projecting light obliquely to the sample, from the first surface side;
   inspecting means for receiving light from the first surface irradiated by said irradiating means and light from the second surface irradiated with light passed through the first surface, to inspect the first and second surfaces;
   inspection control means for setting a time zone for inspection of the first surface so that it does not overlap with the moment at which the light impinges on a boundary between the second surface and the side wall; and
   exposure means for exposing the sample having been inspected by said inspecting means, whereby the pattern of the sample is transferred to the workpiece.

14. An apparatus according to claim 13, wherein said exposure means is adapted to expose the sample having been moved to an exposure position after inspection through said inspecting means.

15. A method, usable with a sample having substantially parallel first and second surfaces coupled by a side wall, for inspecting the state of each surface of the sample, said method comprising:
- an irradiating step for projecting light obliquely to the sample, from the first surface side;
- a first inspecting step for receiving light from the first surface irradiated with the light and light from the second surface irradiated with light passed through the first surface to inspect the first and second surfaces;
- a rotating step for rotating the sample through 180 degrees; and
- a second inspecting step for receiving light from the first surface and light from the second surface irradiated with light passed through the first surface, of the sample having been rotated through 180 degrees, to inspect portions of the first and second surfaces different from those having been inspected before the rotation;
- wherein time zones for inspection of a portion of the first surface to be inspected before rotation and of a portion thereof to be inspected after the rotation are set so that they do not overlap with the moment at which the light impinges on a boundary between the second surface and the side wall.

* * * * *